United States Patent [19]
Lohmann

[11] Patent Number: 5,931,872
[45] Date of Patent: Aug. 3, 1999

[54] PROSTHETIC SOCK FOR REDUCING MOVEMENT BETWEEN RESIDUAL LIMB AND PROSTHESIS AND METHOD FOR USE

[76] Inventor: Klaus H. Lohmann, 345 Barton Hill Rd., Delanson, N.Y. 12053

[21] Appl. No.: 09/039,677

[22] Filed: Mar. 16, 1998

Related U.S. Application Data

[63] Continuation of application No. 08/371,359, Jan. 11, 1995, Pat. No. 5,728,167.

[51] Int. Cl.⁶ ..................................................... A61F 2/78
[52] U.S. Cl. .................................. 623/36; 623/33; 602/62
[58] Field of Search ................................. 623/36, 33, 34, 623/35; 602/63, 62, 61; 128/892; 2/239, 240, 241, 22

[56] References Cited

U.S. PATENT DOCUMENTS

| | | |
|---|---|---|
| 1,319,637 | 10/1919 | Blevens . |
| 1,461,987 | 7/1923 | Smith . |
| 1,497,219 | 6/1924 | Martino . |
| 2,202,598 | 5/1940 | Peterson . |
| 2,646,797 | 7/1953 | Scholl ..................................... 128/165 |
| 3,189,919 | 6/1965 | Chase ............................................ 2/16 |
| 3,322,873 | 5/1967 | Hitchcock ............................... 264/222 |
| 3,520,002 | 7/1970 | Wellington . |
| 3,600,717 | 8/1971 | McKeehan . |
| 3,613,681 | 10/1971 | Adams .................................... 128/293 |
| 3,983,870 | 10/1976 | Herbert et al. .......................... 128/165 |
| 4,341,096 | 7/1982 | Safrit et al. ................................. 66/185 |
| 5,007,937 | 4/1991 | Fishman et al. .......................... 623/34 |
| 5,077,837 | 1/1992 | Meistrell ....................................... 2/16 |
| 5,108,455 | 4/1992 | Telikicherla .............................. 623/33 |
| 5,133,088 | 7/1992 | Dunlap ........................................ 2/241 |
| 5,156,629 | 10/1992 | Shane et al. ............................... 623/37 |
| 5,211,667 | 5/1993 | Danforth ................................... 623/35 |
| 5,226,918 | 7/1993 | Silagy et al. .............................. 623/32 |
| 5,246,464 | 9/1993 | Sabolich .................................... 623/33 |
| 5,258,037 | 11/1993 | Caspers ..................................... 623/36 |
| 5,312,669 | 5/1994 | Bedard .................................... 428/105 |
| 5,376,131 | 12/1994 | Lenze et al. .............................. 623/34 |
| 5,387,245 | 2/1995 | Fay et al. ................................... 623/37 |
| 5,464,443 | 11/1995 | Wilson et al. ............................. 623/37 |
| 5,728,167 | 3/1998 | Lohmann ................................. 623/36 |

FOREIGN PATENT DOCUMENTS 1532625  6/1967  France .

Primary Examiner—Jeffrey A. Smith
Attorney, Agent, or Firm—Heslin & Rothenberg, P.C.; Wayne F. Reinke, Esq.

[57] ABSTRACT

A prosthetic sock for reducing movement of a residual limb within a prosthetic socket of a prosthesis includes a stretchable prosthetic sock having an inner surface and an outer surface, and a movement-opposing material disposed partially on the inner surface and outer surface for reducing the residual limb movement so as to leave areas about a circumference of the prosthetic sock without the movement-opposing material. The prosthetic sock may be a cotton cloth material, and the movement-opposing material may be latex laminated on the inner and outer surface of the sock.

11 Claims, 5 Drawing Sheets

PROSTHETIC SOCK FOR REDUCING MOVEMENT BETWEEN RESIDUAL LIMB AND PROSTHESIS AND METHOD FOR USE

This application is a continuation of U.S. patent application Ser. No. 08/371,359, now U.S. Pat. No. 5,728,167, filed on Jan. 11, 1995.

BACKGROUND OF THE INVENTION

1. Technical Field

The present invention generally relates to prosthetic device accessories. More particularly, the present invention relates to prosthetic socks or sheaths.

2. Background Information

In the past, prosthetic socks have been used by amputees to provide cushioning and a proper fitting for a residual limb within a prosthetic socket of a prosthesis. Typically, a snug-fitting and conforming suction socket sleeve is placed over the residual limb, and covered with one or more prosthetic socks. The prosthetic socks are commonly made of a stretchable material, such as cotton or wool, and are available in different thicknesses from a single ply to multiple plys. Although such prosthetic socks do provide the cushioning and proper fit within the prosthesis, the smoothness of the sock may cause slippage of the residual limb relative to the prosthesis. This movement is especially acute in above-the-knee amputations, however, varying degrees of movement may be found with any residual limb, including arms.

Solutions to this problem have included straps and harnesses to prevent the movement of the residual limb. However, such solutions complicate the process of donning the prosthesis for the amputee, restrict motion and increase discomfort.

Thus, a need exists for a way to reduce movement of a residual limb relative to a prosthesis without adding other mechanisms that complicate the prosthesis donning process.

SUMMARY OF THE INVENTION

Briefly, the present invention satisfies the need for a way to reduce movement of a residual limb relative to a prosthesis without adding additional mechanisms to the prosthesis donning process by providing a prosthetic sock with a movement-opposing material disposed on an inner and outer surface thereof.

In accordance with the above, it is an object of the present invention to reduce the movement of a residual limb relative to a prosthesis for the residual limb.

It is another object of the present invention to provide a prosthetic sock for reducing the movement of a residual limb relative to a prosthesis therefor.

The present invention provides, in a first aspect, apparatus for reducing movement of a residual limb relative to a prosthetic socket of a prosthesis. The apparatus comprises a prosthetic sock fabricated of a first material, and having an inner surface and an outer surface. The apparatus further comprises a movement-opposing material disposed only partially on the inner surface and disposed only partially on the outer surface. The movement-opposing material comprises a second material different from the first material. The movement-opposing material disposed on the inner surface opposes movement of the residual limb relative to the prosthetic sock, and the movement-opposing material disposed on the outer surface opposes movement of the prosthetic sock relative to the prosthetic socket. The movement-opposing material is disposed on the inner surface and the outer surface so as to leave a plurality of areas about a circumference of the prosthetic sock without the movement-opposing material.

The present invention also provides, in a second aspect, a system for reducing movement of a residual limb relative to a prosthetic socket of a prosthesis. The system comprises a suction socket sleeve for placing over the residual limb, the suction socket sleeve conforming to the shape of the residual limb, and apparatus for covering the suction socket sleeve prior to placement within the prosthetic socket. The apparatus comprises a prosthetic sock for placing over the suction socket sleeve, the prosthetic sock being fabricated of a first material and having an inner surface and an outer surface, and a movement-opposing material only partially disposed over the inner and outer surfaces. The movement-opposing material comprises a second material different from the first material. The movement-opposing material disposed on the inner surface opposes movement of the suction socket sleeve relative to the prosthetic sock, and the movement-opposing material disposed on the outer surface opposes movement of the prosthetic sock relative to the prosthetic socket. The movement-opposing material is disposed on the inner surface and the outer surface so as to leave a plurality of areas about a circumference of the prosthetic sock without the movement-opposing material.

The present invention further provides, in a third aspect, a method of using a prosthetic sock to reduce movement of a residual limb relative to a prosthetic socket of a prosthesis. The prosthetic sock is fabricated of a first material and including a movement-opposing material partially disposed over an inner surface and partially disposed over an outer surface thereof, the movement-opposing material comprising a second material different from the first material. The movement-opposing material is disposed on the inner surface and the outer surface so as to leave a plurality of areas about a circumference of the prosthetic sock without the movement-opposing material. The method comprises the steps of: placing a suction socket sleeve over the residual limb, the suction socket sleeve conforming to the shape of the residual limb; placing the prosthetic sock over the suction socket sleeve; and inserting the residual limb with the suction socket sleeve and the prosthetic sock thereon into the prosthetic socket. The movement-opposing material disposed on the inner surface opposes movement of the suction socket sleeve relative to the prosthetic sock, and the movement-opposing material disposed on the outer surface opposes movement of the prosthetic sock relative to the prosthetic socket.

These, and other objects, features and advantages of this invention will become apparent from the following detailed description of the various aspects of the invention taken in conjunction with the accompanying drawings.

BEST MODE FOR CARRYING OUT THE INVENTION

Figure 1:
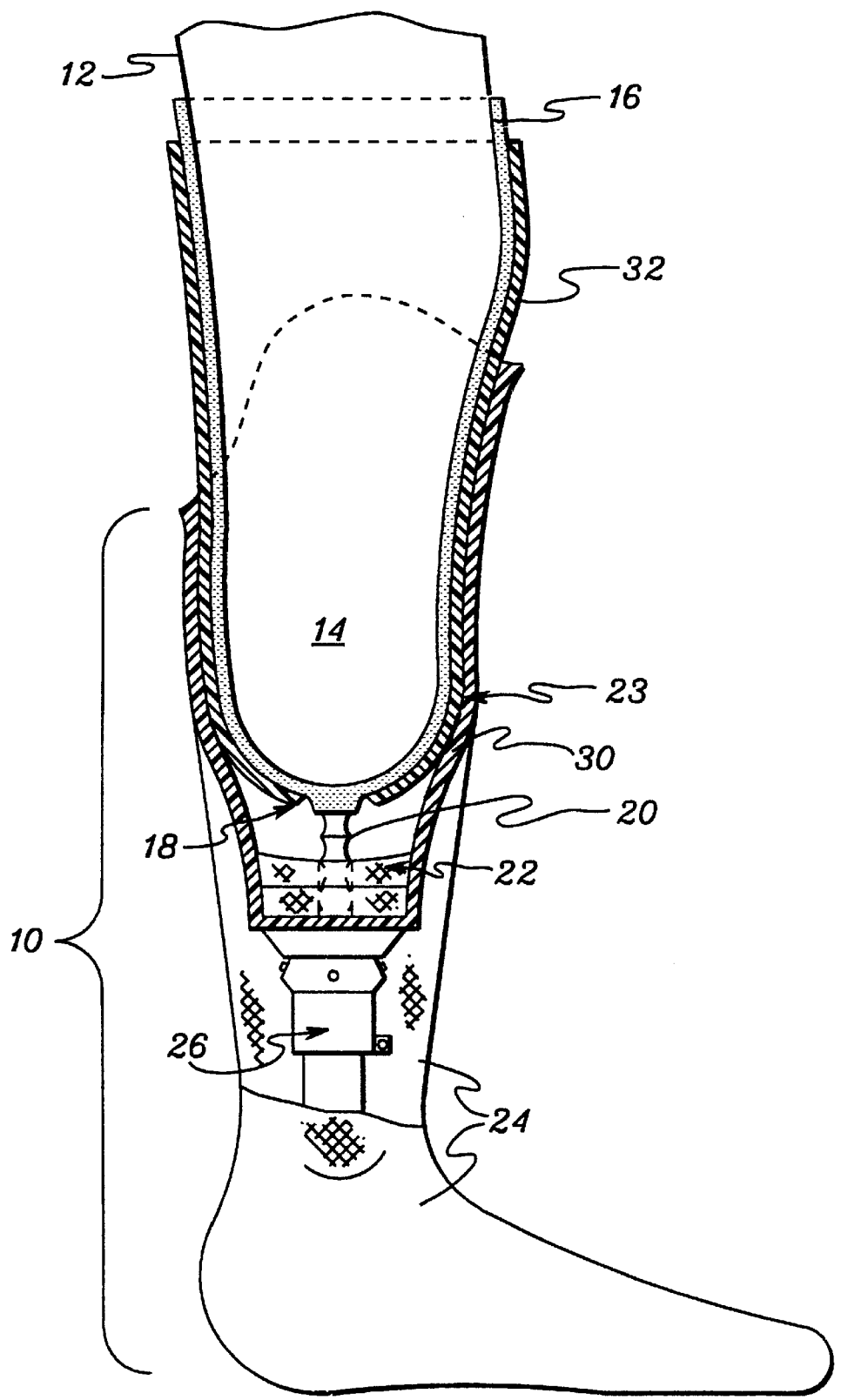
FIG. 1 depicts a residual leg below the knee covered with a suction socket sleeve and prosthetic sock, and placed within a prosthetic socket of a prosthesis including a locking stud and a locking stud mechanism, according to the present invention.

FIG. 1. depicts a prosthesis 10 being worn by a user 12. A residual limb 14 is contained within a suction socket sleeve 16. Sleeve 16 may comprise, for example, silicone, and provides a snug fit about residual limb 14, the shape of sleeve 16 conforming to the shape thereof. Suction socket sleeve 16 is also sometimes referred to as a "roll-on-silicone socket," a "suspension liner" or a "socket insert, suction suspension." Lower end 18 of sleeve 16 is provided in any appropriate manner with a locking stud 20. Locking stud 20 fits within locking stud mechanism 22 and couples thereto such that sleeve 16 stays within prosthetic socket 23 of prosthesis 10. Sleeve 16 is covered with a prosthetic sock 32 having an opening at end 18 for protrusion of the locking stud. Prosthesis 10 is embodied with the shape, size and appearance of a natural lower leg. Accordingly, as is well understood, surface materials 24, such as laminated plastic and foam, are supported on an internal structural frame 26. The lower portion of this support frame may be made of, for example, light-weight metal members, simulating a natural ankle and foot. The upper structural part of prosthesis 10 consists of a rigid plastic cup 30 formed to the shape of the residual limb 14. The lower end of rigid plastic cup 30 is formed about the locking stud mechanism 22 and, thus, effectively serves as a housing therefor.

To accommodate periodic fluctuations in the size of the residual limb 14, due to expansion and contraction thereof, maintain and adjust the compression factors needed for a proper fit, prosthetic socks of varying thicknesses and combinations are used. As used herein, the term "sock" includes what are sometimes referred to as "sheaths", which are very thin socks made of, for example, nylon. These prosthetic socks are pulled over the suction socket sleeve 16. An opening at the distal end of the sock allows the locking stud 20 therethrough to engage the locking stud mechanism 22. One skilled in the art will understand the various ways in which locking stud 20 and locking stud mechanism 22 may be coupled, as well as the various forms they may take.

The use of suction socket sleeves with a locking stud to suspend a prosthetic limb to the residual limb of the amputee provide an excellent vertical suspension force. However, when this method is used for a prosthesis above the knee (see FIG. 4), it becomes difficult to stop or control horizontal rotational movements of the residual limb within the prosthetic socket. Traditionally, ancillary suspension systems, such as belts and straps, have been used to control the rotational movement. Although such systems may decrease the rotational movement, they complicate the donning process for the amputee, restrict motion and increase discomfort. Rather than adding additional mechanisms to the prosthesis donning process, the present invention seeks to provide a new prosthetic sock for reducing or preventing the movement of the residual limb relative to the prosthesis.

Figure 2:
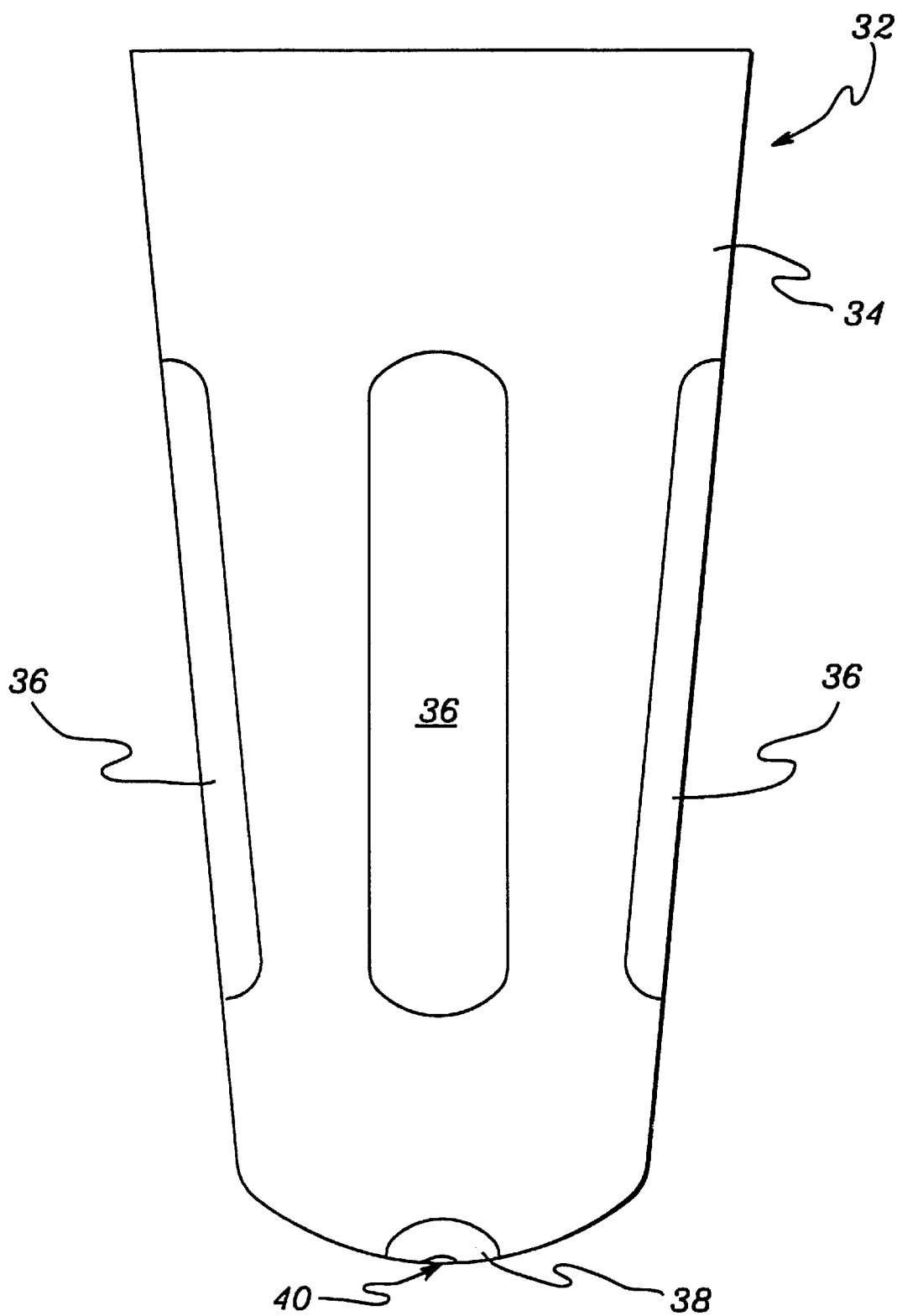
FIG. 2 depicts the prosthetic sock of FIG. 1 in more detail.

FIG. 2 depicts a prosthetic sock 32 according to the present invention. Although described with respect to the residual limb 14 of FIG. 1, it will be understood that the present invention is useful with any type of residual limb on the body, for example, above-the-knee (see FIG. 4) or arms. Prosthetic sock 32 comprises a preferably stretchable material 34, and movement-opposing patch surfaces 36 and 38. Material 34 stretches to conform to the shape of the residual limb, and is preferably made of a material providing comfort and cushioning for the user, such as, for example, cotton. Other possible materials include, for example, wool, acrylic/lycra, polypropolene and rayon. As shown in FIG. 2, movement-opposing patch surfaces 36 comprise a number of spaced vertical strips of a movement-opposing material, such as latex, integral with the stretchable material 34. It will be understood that the inner surface of prosthetic sock 32 also has a movement-opposing patch surface disposed opposite each of the patch surfaces on the outer surface (see FIG. 4). As shown in FIG. 2, there are four such patch surfaces 36, including a patch surface on the back side thereof. Movement-opposing patch surface 38 is toroidally shaped with an opening 40 for passage of locking stud 20. Another such patch surface 38 is oppositely disposed on the inner surface of prosthetic sock 32. Preferably, the use of circumferential patch surfaces (i.e., rings) around stretchable material 34 is avoided, since this may affect the stretching ability of sock 32, requiring an array of different size socks to provide a proper fit.

Figure 3A:
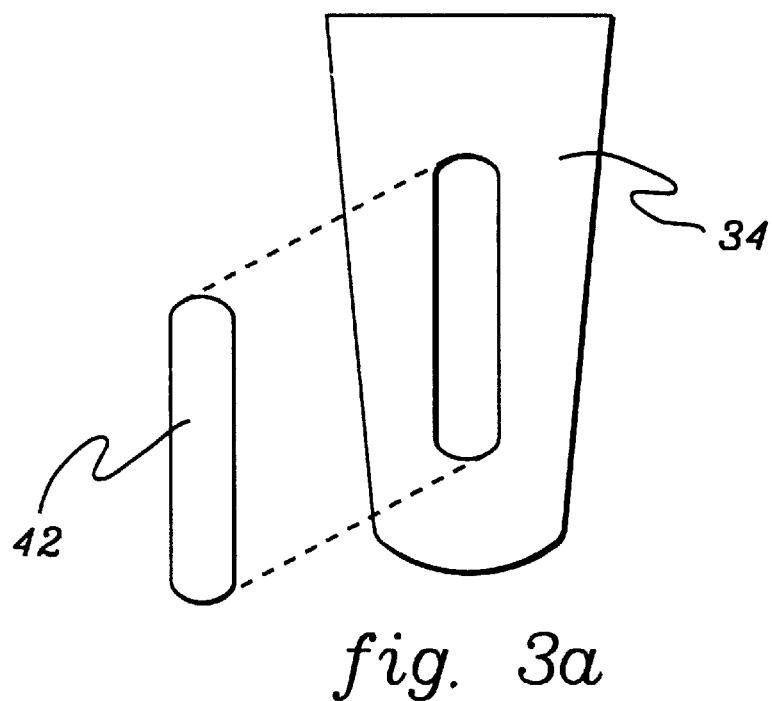
FIGS. 3a and 3b depict an alternate prosthetic sock according to the present invention.
Figure 3B:
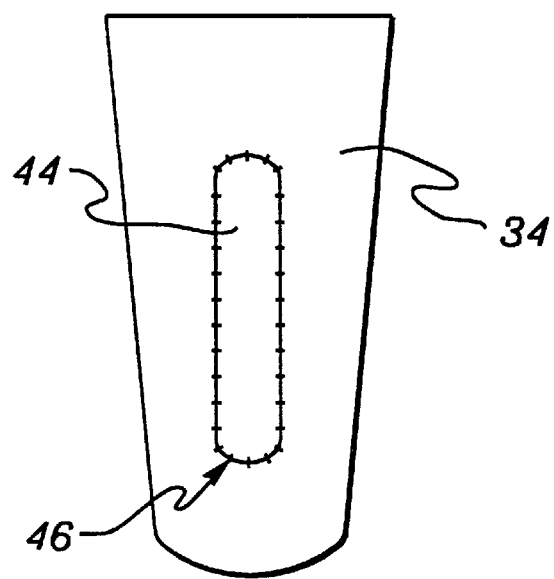

One way to provide movement-opposing patch surfaces 36 and 38 is to laminate a movement-opposing material onto the inner and outer surfaces of the sock so that the inner and outer surfaces are saturated with the movement-opposing material. The preferred use of vertical strips allows normal expansion of the stretchable material 34 and adaptation to the shape of the residual limb. Another way to provide movement-opposing patch surfaces 36 and 38 is to remove a portion 42 of material 34 for insertion of a patch 44, and sew 46 the patch onto the stretchable sock around the periphery thereof (see FIGS. 3a and 3b). When the second method is employed, a single movement-opposing patch provides the movement-opposing surfaces on both the inner and outer surface of the prosthetic sock.

Although shown in FIG. 2 as vertically disposed strips of movement-opposing material, movement-opposing patch surfaces 36 may take a variety of forms, such as a larger number of smaller patch surfaces. In addition, the shape of the patch surfaces may vary. For example, the patch surfaces may have a round shape or a square shape. It will also be understood that a prosthetic sock according to the present invention may not have distinct movement-opposing patches, but could include a sock with a movement-opposing surface on the inside and outside.

Figure 4:
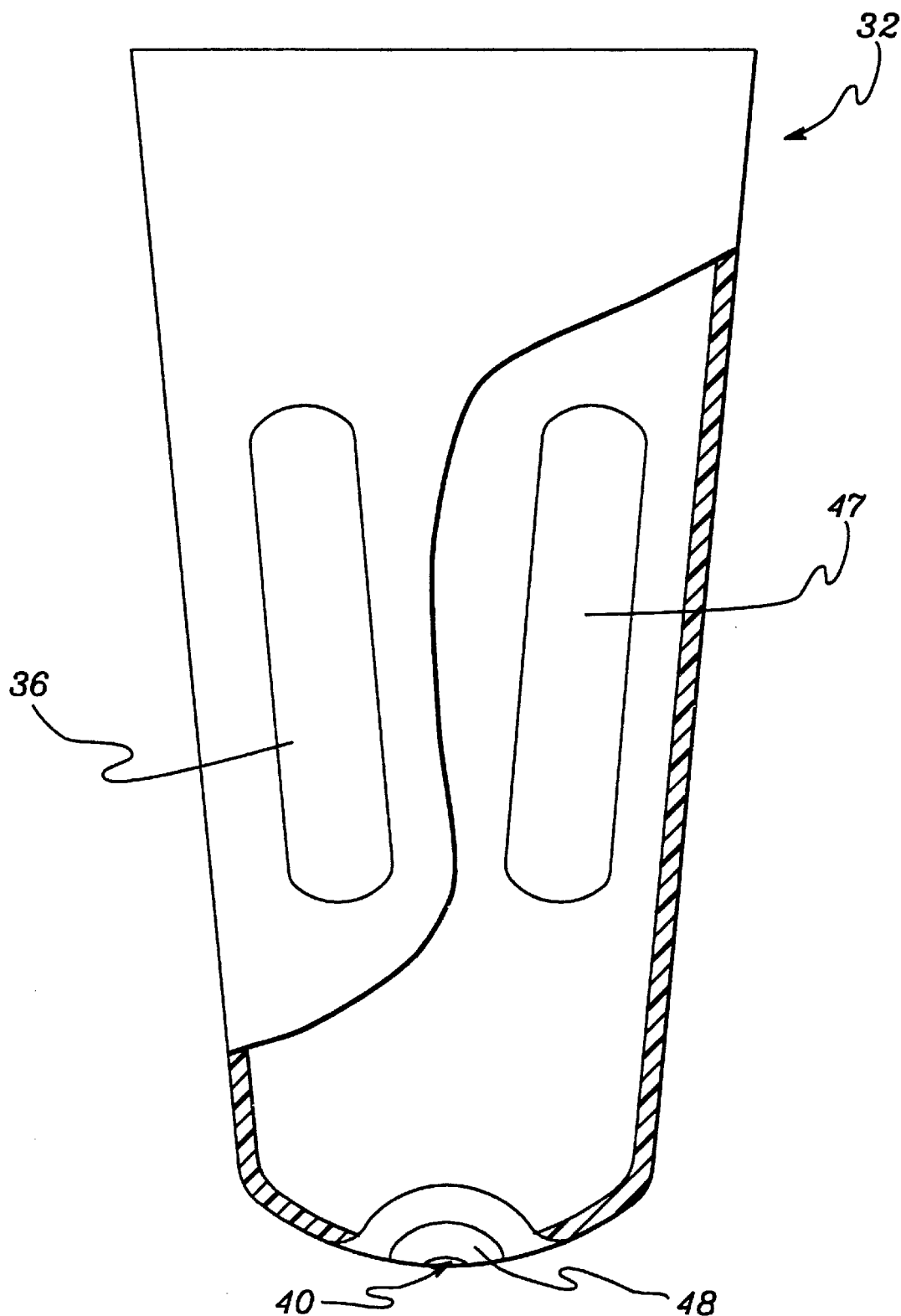
FIG. 4 depicts a partial cut-away view of the prosthetic sock of FIG. 2.

FIG. 4 depicts a partial cut-away view of the prosthetic sock 32 of FIG. 2, including a movement-opposing patch surface 36 on the outside of sock 32 and movement-opposing patch surfaces 47 and 48 on the inside thereof.

Figure 5:
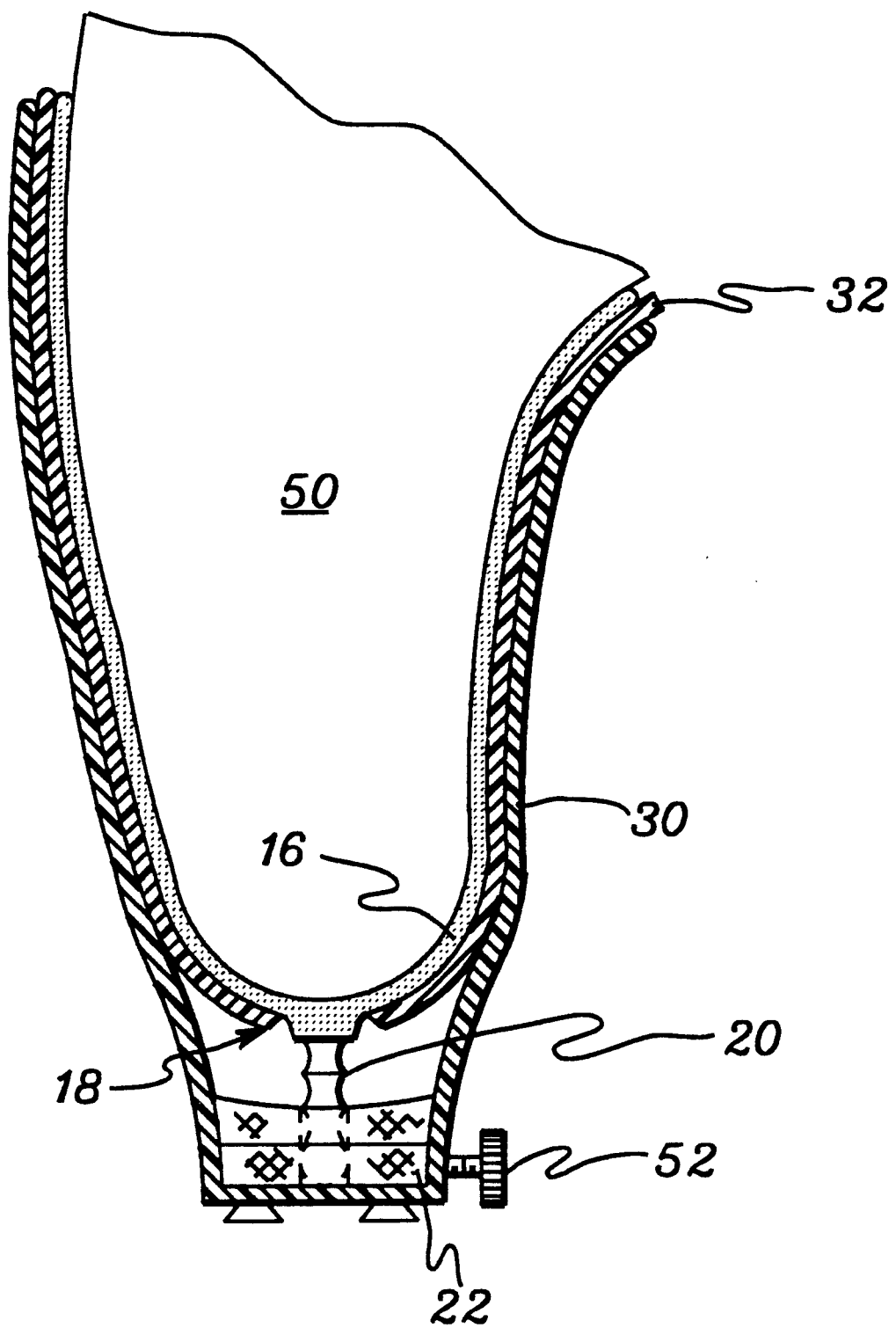
FIG. 5 depicts the apparatus of FIG. 1 used with a residual leg above the knee.

FIG. 5 depicts the relevant portion of the apparatus of FIG. 1 used with a residual leg 50 above the knee, with the addition of screw 52 for locking locking stud 20 within locking stud mechanism 22.

The use of prosthetic sock 32 in the prosthesis-donning process will now be described. More specifically, a amputee first dons the suction socket sleeve, and then pulls prosthetic sock 32 thereover. If prepared prior to donning, a suction socket sleeve may be rolled on from the end of the residual limb toward the body. If the suction socket sleeve includes a locking stud, then an opening in the distal end of the prosthetic sock needs to be aligned therewith. The internal surface of the prosthetic socket 23 is then moistened with water. The moistening allows easy donning of the prosthesis and, as the water evaporates, the movement-opposing patch surfaces provide the friction component to control the rotational movement (and movement in general). To provide the proper thickness, several such prosthetic socks may be combined, donned over each other, to achieve the proper compression factors. When several such socks are combined, the movement-opposing patch surfaces are aligned to preserve the friction component. Alternatively, prosthetic socks of different thicknesses may be used such that the combination of several socks is not necessary.

While several aspects of the present invention have been described and depicted herein, alternative aspects may be effected by those skilled in the art to accomplish the same objectives. For example, the size, shape, number and/or placement of the movement-opposing patch surfaces may vary. As another example, the type of movement-opposing material may vary. As still a further example, the type of material used for the stretchable sock portion of the prosthetic sock may vary. Accordingly, it is intended by the appended claims to cover all such alternative aspects as fall within the true spirit and scope of the invention.

I claim:

1. Apparatus for reducing movement of a residual limb relative to a prosthetic socket of a prosthesis, comprising:

a prosthetic sock fabricated of a first material and having an inner surface and an outer surface; and a movement-opposing material disposed only partially on said inner surface and disposed only partially on said outer surface, said movement-opposing material comprising a second material, said second material being different from said first material of said prosthetic sock, said movement-opposing material disposed on said inner surface opposing movement of said residual limb relative to said prosthetic sock and said movement-opposing material disposed on said outer surface opposing movement of said prosthetic sock relative to said prosthetic socket, wherein said movement-opposing material is disposed on said inner surface and said outer surface so as to leave a plurality of areas about a circumference of said prosthetic sock without said movement-opposing material.

2. The apparatus of claim 1 wherein said prosthetic sock comprises a stretchable cloth material.

3. The apparatus of claim 2 wherein said stretchable cloth material comprises cotton.

4. The apparatus of claim 1 wherein said plurality of movement-opposing material comprises latex.

5. The apparatus of claim 1 wherein said movement comprises rotational movement.

6. A system for reducing movement of a residual limb relative to a prosthetic socket of a prosthesis, comprising:

a suction socket sleeve for placing over said residual limb, said suction socket sleeve conforming to the shape of said residual limb; and apparatus for covering said suction socket sleeve prior to placement within said prosthetic socket, comprising:

a prosthetic sock for placing over said suction socket sleeve, said prosthetic sock being fabricated of a first material and having an inner surface and an outer surface, and a movement-opposing material only partially disposed over said inner surface and said outer surface, said movement-opposing material comprising a second material, said second material being different from said first material of said prosthetic sock, wherein said movement-opposing material disposed on said inner surface opposes movement of said suction socket sleeve relative to said prosthetic sock and wherein said movement-opposing material disposed on said outer surface opposes movement of said prosthetic sock relative to said prosthetic socket, wherein said movement-opposing material is disposed on said inner surface and said outer surface so as to leave a plurality of areas about a circumference of said prosthetic sock without said movement-opposing material.

7. The system of claim 6 wherein said suction socket sleeve comprises a silicone suction socket sleeve.

8. The system of claim 6 wherein said prosthetic sock comprises a stretchable cloth material.

9. The system of claim 8 wherein said stretchable cloth material comprises cotton.

10. The system of claim 6 wherein said movement comprises rotational movement.

11. A method of using a prosthetic sock to reduce movement of a residual limb relative to a prosthetic socket of a prosthesis, said prosthetic sock being fabricated of a first material and including a movement-opposing material partially disposed over an inner surface and partially disposed over an outer surface of said prosthetic sock, said movement-opposing material comprising a second material, said second material being different from said first material, wherein said movement-opposing material is disposed on said inner surface and said outer surface so as to leave a plurality of areas about a circumference of said prosthetic sock without said movement-opposing material, said method comprising the steps of:

placing a suction socket sleeve over said residual limb, said suction socket sleeve conforming to the shape of said residual limb;

placing said prosthetic sock over said suction socket sleeve, wherein said movement-opposing material disposed on said inner surface opposes movement of said suction socket sleeve relative to said prosthetic sock and wherein said movement-opposing material disposed on said outer surface opposes movement of said prosthetic sock relative to said prosthetic socket; and inserting said residual limb with said suction socket sleeve and said prosthetic sock thereon into said prosthetic socket.

* * * * *